United States Patent [19]
Lormeau et al.

[11] Patent Number: 4,486,420
[45] Date of Patent: Dec. 4, 1984

[54] MUCOPOLYSACCHARIDE COMPOSITION HAVING A REGULATORY ACTION ON COAGULATION, MEDICAMENT PROCESS FOR PREPARATION AND METHOD OF USE

[75] Inventors: Jean C. Lormeau, Maromme La Maine; Jean Choay, Paris; Jean Goulay, deceased, late of Oissel; Marie T. Goulay, heir; Marie A. Goulay, heir, both of St. Pierre de Varangeville; Gerard Goulay, heir, Saind Amand des Hautes Terres, all of France

[73] Assignee: Choay, S.A., Paris, France

[21] Appl. No.: 301,611

[22] Filed: Sep. 14, 1981

Related U.S. Application Data

[63] Continuation-in-part of Ser. No. 204,505, Nov. 6, 1980, which is a continuation of Ser. No. 091,164, Nov. 5, 1979, abandoned.

[30] Foreign Application Priority Data

Nov. 6, 1978 [FR] France ................................ 78 31357
Jul. 20, 1979 [FR] France ................................ 79 18873

[51] Int. Cl.³ ..................... A61K 31/727; C08B 37/10
[52] U.S. Cl. ........................................ 424/183; 536/21
[58] Field of Search ........................... 424/183; 536/21

[56] References Cited

U.S. PATENT DOCUMENTS

| | | | |
|---|---|---|---|
| 4,168,377 | 9/1979 | Choay et al. | 424/183 |
| 4,175,182 | 11/1979 | Schmer | 536/21 |
| 4,281,108 | 7/1981 | Fussi | 424/183 |
| 4,303,651 | 12/1981 | Lindahl et al. | 424/183 |
| 4,315,923 | 2/1982 | Takacs et al. | 424/183 |

*Primary Examiner*—Johnnie R. Brown
*Attorney, Agent, or Firm*—Weiser & Stapler

[57] ABSTRACT

The invention pertains to a mucopolysaccharide fraction obtainable from heparin or from fractions including heparinic constituents of molecular weights from 2,000 to 50,000, which has a Yin-Wessler titer which is high relative to the USP titer. It contains components whose molecular weights are less than 10,000, particularly oligosaccharides in the area of 2,000–3,000, comprising from 8 to 12, notably 10 monosaccharide units, among which glucosamine units whose primary positions are sulphated. The last mentioned oligosaccharides include one N-acetyl-glucosamine unit per two units of 2-0-sulphate iduronic acid and per two N-sulphate-glucosamine units, the other saccharide units being of a different nature and including distinct substituents.

29 Claims, 16 Drawing Figures

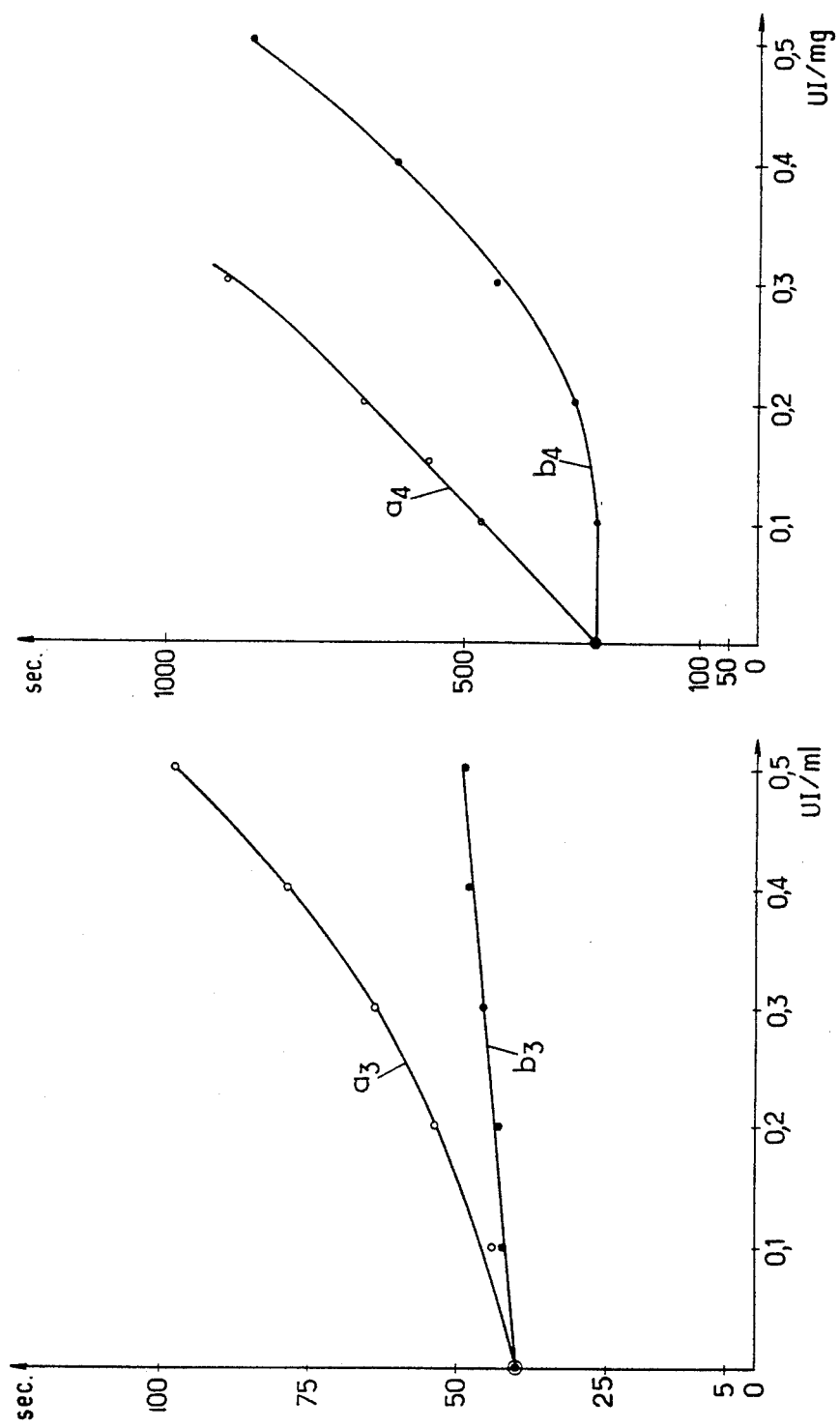

MUCOPOLYSACCHARIDE COMPOSITION HAVING A REGULATORY ACTION ON COAGULATION, MEDICAMENT PROCESS FOR PREPARATION AND METHOD OF USE

This application is a continuation-in-part application of our co-pending application Ser. No. 204,505 pending filed Nov. 6, 1980, which was a continuation of the co-pending application Ser. No. 091,164 now abandoned filed Nov. 5, 1979.

The invention relates to a mucopolysaccharide fraction endowed with biological properties, enabling it notably to play a regulator role with respect to blood coagulation. Such a fraction can notably be obtained from heparin preparations, such as mammalian tissue extracts.

Certainly heparin is doubtless until now one of the most important anticoagulant medicaments, if not the most important, available to the clinician. It is in fact capable of taking part at several levels in cascades of successive enzymatic reactions, which are normally engaged in the course of physiological hemostasis, in any situation capable of resulting in hypercoagulability of the blood. It is more particularly capable of simultaneously depressing a large number of the coagulation factors participating to the creation and the up keeping of different forms of hypercoagulability.

There will be recalled below, within the limits necessary for clarity of the description, some of the basic notions, purposely expressly simplified, relating to coagulation. The coagulation process comprises in fact three phases generally described as successive, even if they are intricly interrelated:
thromboplastin formation, the phase of prothrombinase (or active thromboplastin) formation,
thrombin formation, which phase can be summarized as the conversion of the prothrombin into thrombin under the influence of prothrombinase in the presence of ionized calcium and finally,
fibrin formation, the phase in the course of which the blood fibrogen is, under the effect of the thrombin, converted into fibrin, which protein tends to become insoluble.

The formation of prothrombinase occurs, in the course of the thromboplastin formation step essentially according to two different routes: the intrinsic or endogenic route, and the extrinsic or exogenic route, which end in the formation of prothrombinases of respectively plasmatic and tissular origins, both capable of activating prothrombin into active thrombin.

The intrinsic or endogenic route (or system) involves a large number of factors or plasmatic proenzymes capable of being successively activated (factors XII, XI, IX, VIII and X), where each activated product (factors XIIa, XIa, IXa, VIIIa and Xa) acts like an enzyme capable of activating the following proenzyme, the activated X factor (Xa) then taking part, notably by reaction with the V factor and a phospholipid of platelet origin, in the production of active endogenic plasmatic prothrombinase. The extrinsic or exogenic system, which can notably be directly dependent of a tissular lesion, calls upon a more limited number of factors and includes notably the production of tissular thromboplastin which, in combination with the VII factor, can, just as the factor VIIIa, convert the inactive X factor into the Xa factor. The activation sequence of the prothrombin into thrombin is then substantially the same as for the intrinsic system, but the phospholipid is here of tissular and not of plasmatic origin.

It is hence possible, to some limited extent to express the idea that the two intrinsic and extrinsic routes join each other at the level of the activation of the X factor (also called Stuart factor), the two following phases of coagulation—thrombin formation and fibrin formation, no longer then giving rise to a distinction between the intrinsic and extrinsic routes.

The outcome of the coagulation process consists in the formation of an insoluble fibrin clot, intended notably to fill in the lesion at the origin of the triggering of this process, for example at the level of a blood vessel.

These coagulation processes normally give rise then to a process, called fibrinolysis, intended to produce lysis of the clot, notably under the effect of plasmin, which enzyme only exists normally in the circulating blood in the form of an inactive precursor, plasminogen, the fibrin itself constituting nonetheless one of the factors capable of initiating the conversion of the inactive plasminogen into fibrinolytically active plasmin.

In fact, although there has, in the foregoing, been presented systems of coagulation and of fibrinolysis as two processes occurring successively in time, it is still not normally so in reality. In fact, there are involved balanced mechanisms, according to extremely complex processes, under the dependence of harmoniously opposed activator and inhibitor factors. The unbalance of these mechanisms, in the sense of hypercoagulability, is then capable of resulting in thromboses. On the other hand, a disequilibrium in the sense of hypocoagulability, exposes the host to hemorragic risks.

It is obviously to palliate the effects of hypercoagulability that recourse is currently had to the powerful anticoagulant properties of heparin, in order to bring back the coagulation-fibrinolysis mechanism to equilibrium, each time that the latter is subjected to a considerable disturbance, for example on the occasion of a surgical operation on the host. It is however well known that these attempts at re-equilibration are extremely delicate and that, consequently, the administration of too high a dose of anticoagulant medicament—or the insufficient selectivity of the latter—for the purpose of preventing the risks of hypercoagulation, for example the appearance of post-operative thromboses, may finally be at the origin of serious hemorragies: whence the necessity of constant watch of the treated patients and of the necessary adjustments of the doses administered—continuously or discontinuously—according to the results of tests, notably of overall coagulability, like the Howell time, which must be practiced at regular intervals.

It is hence an object of the invention to provide active principles of medicaments (and the medicaments themselves) capable of overcoming these difficulties at least in part, notably which are capable of permitting a possible re-equilibration and/or easier control, at the cost of a lesser clinical watch of the coagulation-fibrinolysis system in patients afflicted with a pathology of the coagulation which have undergone a treatment, such as a surgical operation, which expose them to risks of hypercoagulability.

The invention relates more particularly to a mucopolysaccharide fraction exerting a regulator effect with regard to coagulation, notably in causing it to be delayed, yet upon bringing into play inhibitoryactions which are more selective than those of heparin, with respect to a smaller number of coagulation factors, more particularly with respect to the activated X factor.

The invention hence relates to a mucopolysaccharide fraction obtainable from heparin or from fractions including heparinic constituents of molecular weights extending notably from about 2,000 to 50,000, such as obtained by extraction from mammalian tissues, this fraction being characterized in that it is soluble in an aqueous-alcoholic medium (water-ethanol) having a titer of 55°–61° GL, in that it tends to insolubility in a water-ethanol medium having a higher alcohol content, in that it is insoluble in pure alcohol, and in that it has a Yin-Wessler titer and a USP titer which are respectively in a ratio at least equal to 2, notably at least 3, preferably higher than 6.

These mucopolysaccharide fractions give rise to supplementary fractionations, enabling the preparation of mucopolysaccharide fractions of high specific activity, at the level of the Yin-Wessler titer and having ratios of the Yin-Wessler titer to the USP titer exceeding 10, even 16.

The Yin-Wessler titer is measured by the technique of these authors which is described in "J. Lab. Clin. Med.", 1976, 81, 298–300.

The USP titer, which measures, in manner known in itself, an overall coagulation intensity under well determined conditions, is well known. It is recalled that it is determined in the manner described in the Pharmacopea of the United States XIX, pp. 229–230, (see also the Second Supplement USP-NF, p.62, and the Fourth Supplement USP-NF, p. 90, respectively entitled "Drug Substances and Dosage Forms".

The invention provides a particularly interesting active principle owing to the capacity that it has of inhibiting the Xa factor in a manner which may be very selective, which capacity contrasts with its activity on the overall coagulation, which may be maintained at a very low level.

This mucopolysaccharide fraction hence constitutes a particularly advantageous anticoagulant medicament active principle, to the extent that it may to this day be admitted that a preferential inhibition of an activated factor, occuring at a stage closer to thrombin formation practically at the intersection of said intrinsic and extrinsic routes and downstream thereof, is liable of ensuring protection against the risk of hypercoagulability, equivalent to that procured by heparin currently used in therapeutics, without however, by reason of this selectivity of action, resulting in the same hemorragic risks as those of conventional heparin. The latter is in effect adapted to inhibit not only the Xa factor, but also other factors coming into play both upstream and downstream of the latter, at other stages of the coagulation routes, for example the factor IIa. It is believed that the re-equilibration in vivo of the coagulation and fibrinolysis system, when the latter tends to become unbalanced under the effect of a pathological cause or of an external operation, for example surgery is easier to achieve with a medicament acting selectively on a specific factor, the factor X, more particularly at the level of inhibition of the factor Xa, than with a medicament capable of acting in un-differentiated manner on several coagulation factors at once.

The invention relates also to a process for obtaining such a mucopolysaccharide fraction, this process comprising:

suspending in an aqueous alcoholic medium of the water-ethanol type, having a titer comprised between about 55° and about 61° GL, preferably of the order of 58° GL, of a substance based on heparin or heparinic constituents whose molecular weights range notably from 2,000 to 50,000, this substance having a low content of inorganic salts, preferably less than 1% by weight, separating the insoluble fraction and recovering the solution containing the dissolved mucopolysaccharide fraction, from which it can in its turn be separated, notably by alcoholic precipitation, from the above-mentioned aqueous alcohol medium.

The starting material, from which the mucopolysaccharide according to the invention may be extracted, may be constituted by a heparin of conventional, injectable pharmaceutical quality, or by a crude heparin such as is obtained at the end of extraction operations for this active principle from tissues or organs of mammals, notably from intestinal mucous or from lungs, for example of pork or beef. It can also be constituted by fractions which are normally discarded (waste) in the purification of such crude heparin, for obtaining a heparin of injectable quality and of higher specific activity, provided of course that the waste materials of lower specific activity still contain heparinic constituents.

It is then possible, from raw materials of this type, substantially free from proteins, from nucleic acids and from inorganic salts, preferably when the contents by weight of the latter are less than 1%, to obtain by extraction with 55°–61° GL alcohol a mucopolysaccharide fraction containing constituents of low molecular weight, of which the Yin-Wessler and USP titers are in a ratio of about 2 to about 5, notably from 3 to 5.

It may be remarked that in using water-ethanol mixtures having more than 61° GL, the extraction yield becomes practically zero. On the other hand, the use of aqueous-alcoholic medium of a titer less than 55° GL results in the solubilization of constituents whose presence leads to the lowering of the ratio of the Yin-Wessler/USP titers.

It is to be noted that it is possible to proceed with additional fractionations of the mucopolysaccharide fraction obtained at the end of the above-mentioned process, by various techniques, such as gel-filtration or again selective precipitation in an aqueous-alcoholic medium of predetermined titer, in the presence of proportions also predetermined of an inorganic salt, such as sodium chloride.

An additional fractionation may be achieved by a supplementary step applied to each mucopolysaccharide fraction, previously redissolved in water, which step consists of adding to this aqueous solution from 1 to 2 volumes of ethanol and from 10 to 100 g/l of sodium chloride and of collecting, on the one hand, the equally active precipitate formed and, on the other hand, the content remaining dissolved in the supernatant liquor, notably by a further alcoholic precipitation, and which constitutes a fractionation product whose Yin-Wessler and USP titers respectively are in a ratio still higher, of the order of 6 to 8, than that relating to the initial fraction, notably of the order of 3.

Mucopolysaccharide fractions having a ratio of Yin-Wessler/USP titers which are higher can also be obtained by gel-filtration from the fractions of the first extraction by the 55°–61° GL aqueous-alcohol medium, after prior redissolution of the latter fractions in an aqueous solvent, such as a 0.5M NaCl; 0.1M tris-HCl solution at pH 7.5. Such a solution may be passed through a gel of polyacrylamide and agarose, in bead form, having the tradename ULTROGEL AcA 44, whose effective fractionating zone is situated between effective molecular weights of 4,000 to 60,000 (for linear molecules).

Mucopolysaccharide fractions of the invention, which have a higher Yin-Wessler/USP titer-ratios, are those in which flow after the elution of a volume of 2.5 liters, dead volume not included (the dead volume being the volume of liquid contained in the column of gel, notably in the interstitial spaces between the grains of gel), when the gel-filtration is carried out, with a flow rate of 200 ml/hour, in a column having a diameter of 100 mm and a height of 1 m and when the concentration of mucopolysaccharide and the volume of solution placed on the column have been respectively 50 mg/ml and 37.5 ml. The most active fractions are then contained in the 1.5 liters which flow subsequently. The content of the first 2.5 liters is to a great extent formed from heparane-sulphates or heparitine-sulphates, products of higher molecular weight and of high viscosity, which do not have anticoagulant activity.

The passage from one column to another column of the same length but of different cross-section entails modification of the volume of solution (of the same concentration) to be placed on the other column, with respect to the volume placed on the preceding column, in a ratio equal to the square of that of the cross-sections (or diameters) of these columns, in order that the same fractions may be obtained in an elution volume from the other column itself also occuring in a ratio with the corresponding elution volume of the preceding column substantially equal to the square of the ratio of said cross-sections.

Gel-filtrations of this type also have the additional advantage, apart from that which resides in the production of fractions in which the ratio of the Yin-Wessler-/USP titers is more favorable, of providing products whose solutions have low viscosity.

In this respect, it should be noted also, that the process according to the invention of extraction of mucopolysaccharide fractions by means of a 55°–61° GL, preferably 58° GL alcohol solution, from a commercial or purified heparin, notably of injectable quality, still containing notably proportions of heparane-sulphates or similar products with high molecular weight, also constitutes in itself a process enabling the reduction in considerable proportions of the viscosity of the aqueous solutions, which can then be formed from these heparins, then essentially free from these mucopolysaccharide fractions.

This reduction in viscosity presents a certain advantage, having regard to the subsequent application of such heparins in anticoagulant therapy, by parenteral, notably sub-cutaneous injection.

From fractions having ratios of Yin-Wessler/USP titers of the order of 6 to 8, it is possible to obtain, by additional fractionations, notably by gel filtration or the like, mucopolysaccharide fractions characterized by ratios of Yin-Wessler/USP titers exceeding 10, notably of the order of 13–16, and having Yin-Wessler titers higher than 130, notably 135 to 160 units/mg.

It is understood that the foregoing indications of molecular weights (and which also follow, notably in the examples) are derived from measurements of the retention time of solutions having a predetermined content of the substance studied, in experiments of gel permeation through a column of gel, under equally predetermined elution conditions, the logarithms of these molecular weight indications being in the same relationship of proportionality with respect to the above-said measurements of retention time, as are those of the molecular weights of 4,000, 6,500, 16,000, 31,000 respectively, of polystyrene-sodium sulphonate standards, notably those marketed by the company named CHROMPACK (Orsay-les-Ulis, France), with respect to their respective retention times, measured in a system and under gel-permeation conditions which are identical.

To the extent where the treated fractions, whatever the degree of purification reached, are in the state of physiologically acceptable metallic salts, such as those of sodium, they may then be converted into mixed or simple salts containing another physiologically acceptable metal, such as calcium, by any process applicable to the salts of heparin. Advantageously, it is possible to resort to the process described in French Pat. No. 73 13580 filed Apr. 13, 1973, by Applicant. It will be recalled that this process consists essentially, starting, for example, from a sodium salt of heparin, of contacting the latter with a different salt of another physiologically acceptable metal, for example calcium chloride, in solution, of then proceeding with the separation of the metallic ions unbound to the heparin (for example by alcoholic precipitation or dialysis) and, to the extent that the substitution ratio reached is not sufficient, of recontacting, in solution, the mixed heparin salt obtained at the end of the first contacting, with a further amount of another salt, notably calcium chloride, according to the desired final substitution ratio.

A further preferred MPS fraction of the present invention can further be obtained from one or the other hereabove described fractions, which further fractions are characterized:

in that, in a gel-filtration operation on a gel column of polyacrylamide and agarose, in bead form, of the type marketed under the name ULTROGEL AcA 44, this fraction flows through after elution of a volume of 2.5 liters, dead volume not included, when the gel-filtration is conducted, at a flow rate of 200 ml/hour, in a column having a diameter of 100 mm and a height of 1 m and when the concentration of the mucopolysaccharide and the volume of the solution placed on the column have been respectively 50 mg/ml and 37.5 ml, the essential of this fraction being notably contained in the 1.5 liters of eluate which then flow through, by a retention time of the order from 5.7 to 7.5, notably from 6.6 to 7.0 minutes in a gel-permeation system on a column filled with silica of granulometry from 10 to 100 microns, of 250 mm in height and 9 mm diameter, when 50 μl of a solution of 1.3 mg/ml of this fraction in a 0.02M $Na_2SO_4$ buffer, having been placed on this column, the elution of said fraction at a flow rate of 3 ml/minute then follows.

Preferred fractions according to the present invention are characterized more particularly again, on the one hand, by a particular affinity with regard to antithrombin III manifested by their capacity to be fixed on the latter, notably in a system comprising the contacting of the fractions with an antithrombin III fixed on a support, such as agarose, in an 0.2M NaCl, 0.05tris-HCl buffer at pH 7.5 and, on the other hand, by Yin-Wessler and USP titers which are in the ratio (YW/USP ratio) at least equal to 6, the Yin-Wessler titer itself being at least equal to 300 U/mg.

Preferred fractions and compounds according to the invention are characterized by YW/USP ratios higher than 18, with a Yin-Wessler activity higher than 900 U/mg.

Preferably again the fractions and compounds according to the invention are characterized by YW/USP ratios higher than 50.

The preferred compounds of the invention are characterized by YW/USP ratios higher than 65 with a Yin-Wessler activity higher than 1,300 U/mg.

The particular affinity of the fractions according to the invention for Antithrombin III is an essential property to be relied upon for producing such highly enriched fractions, notably from the preceding ones, which process consists of effecting selective fixation of the further enriched fractions or products of the present invention on antithrombin III, notably by contacting the initial fractions with immobilized antithrombin III, particularly on a support, notably agarose, in a buffer such as 0.2M NaCl, 0.05M tris-HCl at pH 7.5, and then eluting the fixed fraction with a buffer of higher ionic force, sufficient to produce desorption, notably a 2M NaCl, 0.05M tris-HCl buffer.

Of course, the starting material from which the last mentioned fractions or compounds are obtainable are not limited to the first fractions according to the invention which have been defined above. Particularly they may be obtained in any other suitable manner, notably from the crude starting material whose nature has been recalled above and from which said first fractions themselves were obtained.

The invention relates more particularly also to the substantially homogeneous compounds and in state of substantial purity which appear to constitute the essential active principle of the preceding fractions.

These compounds are characterized by nuclear magnetic resonance spectra (NMR) carried out under the conditions indicated below and which are the subject of FIGS. 11, 12, 14 and 15.

Referring more particularly to the NMR spectrum of the compounds according to the invention for the proton ($^1$H) carried out on solutions of these compounds dissolved in deuteriated water at 35° C. with a radiation of 270 megahertz (MHz) there are observed as characteristic element of the spectrum, resonance signals which, for chemical displacement of the order of 4.8 and 5.2 ppm, are substantially weaker than the resonance signal which is also observed for a chemical displacement of the order of 5.4 ppm (reference for the measurement of the displacements: TSP (sodium 3-trimethylsilyl propionate 2,2, 3,3-d4)).

The signals observed at the level of the chemical displacements of 5.4; 5.2 and 4.8 ppm correspond to the signals which, in the case of a conventional heparin studied by NMR under the same conditions, are respectively characteristic of the:
- anomer proton, in the 1 position, of the glucosamine N-sulphated units of heparin (signal $G_1$);
- anomer proton in the 1 position, of 2-O-sulphated iduronic acid units (signal $I_1$) and
- proton in the 5 position of 2-O-sulphated iduronic acid units (signal $I_5$).

In conventional heparins, the ($G_1$), ($I_1$) and ($I_5$) signals have all three intensities of the same order of magnitude.

For convenience of language, reference will also be made below, even as regards the fractions or compounds according to the invention, to the signals ($G_1$), ($I_1$) and ($I_5$), to denote the signals observed in relationship with the corresponding chemical displacements (whether for the proton or for $^{13}$C).

This equivalence of language will also extend to the NMR spectrum produced under different conditions and with different references.

Referring more particularly to the NMR spectrum of the compounds according to the invention for carbon 13 ($^{13}$C), effected on solutions of these compounds dissolved in deuteriated water with a radiation of 20 MHz, there are observed as characteristic elements of the spectrum (reference for the measurement of the TMS (tetramethylsilane)):
- the absence practically of the resonance signal characteristic of the presence of OH groups on the primary carbon (in the 6 position) of the glucosamine units contained in the mucopolysaccharide fractions of the invention,
- additional signals, in the region of the ($I_1$) and ($G_1$) signals, in regions corresponding to chemical displacements of the order of 100 ppm,
- an additional ($G_2$) signal close to the $G_2$N-sulphate signal in the 60 ppm region,
- the presence of a resonance signal in the 75 ppm region (to which normally substantially no resonance signal corresponds in the NMR spectra obtained under similar conditions with a conventional heparin), (the indications of chemical displacements indicated above are estimated with respect to the CH$_3$ of the N-acetyl glucosamine groups contained in the MPS according to the invention (25 ppm region in the spectra of the drawings)).

The homogeneous compounds according to the invention, in the practically purified state, which all have the characteristics which have been described already above, as regards their USP and Yin-Wessler activities and their specific affinities for antithrombin III, are also characterized in that they are formed by a homogeneous oligosaccharide having again the following additional characteristics:
- it comprises from 8 to 12, notably 10 monosaccharide units;
- all the primary positions of the glucosamine units of this oligosaccharide are sulphated;
- this oligosaccharide comprises one N-acetyl glucosamine unit for two 2-O-sulphate iduronic acid units and for two N-sulphate-glucosamine units, the other saccharides being of a different nature and including separate substitutents.

The molecular weights of certain at least of the oligosaccharides according to the invention are situated in a range from about 2,000 to about 3,000, notably from about 2,500 where decasaccharides are concerned.

The invention relates also to polysaccharides having the above-indicated general properties, as regards more particularly the USP and Yin-Wessler activities, on the one hand, and the affinity for antithrombin III, on the other hand, these fractions having a higher molecular weight, but also containing in their structure an oligosaccharide part having the above mentioned structure.

Other characteristics of the invention will appear also in the course of the description which follows of preferred examples of the practising of the invention, notably with reference to the drawings in which:

FIGS. 2 to 7 show the comparative biological properties of mucopolysaccharide fractions according to the invention and of a conventional heparin with high anticoagulant activity (in USP titer).

EXAMPLE 1

The raw material was constituted by 100 g of an injectable heparin having a titer of 170 IU/mg (USP units).

To this 100 g of heparin, 2,500 ml of 58° GL alcohol are added. After very vigorous stirring for 15 minutes, vigorous stirring is continued for 15 hours. The suspension is then centrifuged at 7,000 rpm for 1 hour and the supernatant liquor is recovered: 2,400 ml.

To this supernatant liquor 80 ml of saturated sodium chloride solution and then 2,400 ml of 100° GL alcohol are then added.

The precipitated product is recovered, washed with alcohol and dried. It weighs 2.1 g.

It will be called hereafter LMF (low molecular weight fraction). Results regarding the physical and chemical properties of this fraction are given herebelow.

Results obtained with commercial heparin, i.e. unfractionated heparin (designated U H) are given for purpose of comparison.

I—Physical and chemical properties (1°) molecular weight (HPLC method)

L M F: 4,000–8,000 U H: 4,000–30,000

(2°) analytical results

Sulfate, N-acetyl glucosamine, glucuronic acid and iduronic acid content of LMF and UH were determined. The results are given in Table I.

TABLE 1

|  | LMF | UH |
| --- | --- | --- |
| SULFATE | 26% | 34% |
| N—ACETYL GLUCOSAMINE | 7% | 3% |
| GLUCURONIC ACID | 11% | 6% |
| IDURONIC ACID | 24% | 24% |

It appears from these results that the LMF has a content in N-acetyl glucosamine and acid glucuronic moieties higher than heparin. The content in iduronic acid units appears to be similar. The sulfate content is somewhat less than in heparin.

(3°) N M R spectrum

Figure 1:
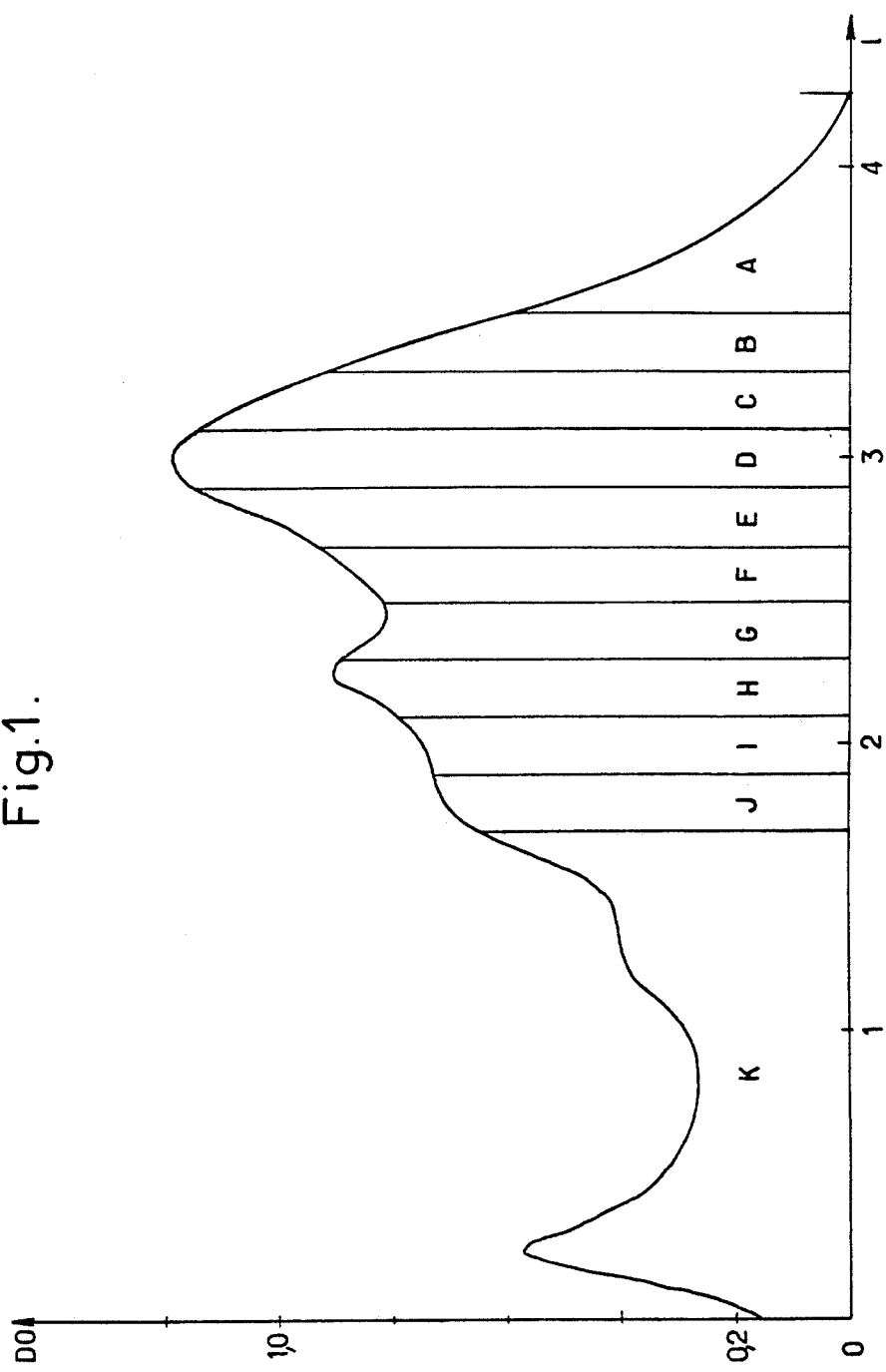
FIG. 1 shows a characteristic elution diagram of a preferred mucopolysaccharide fraction, according to the invention.
Figure 1A:
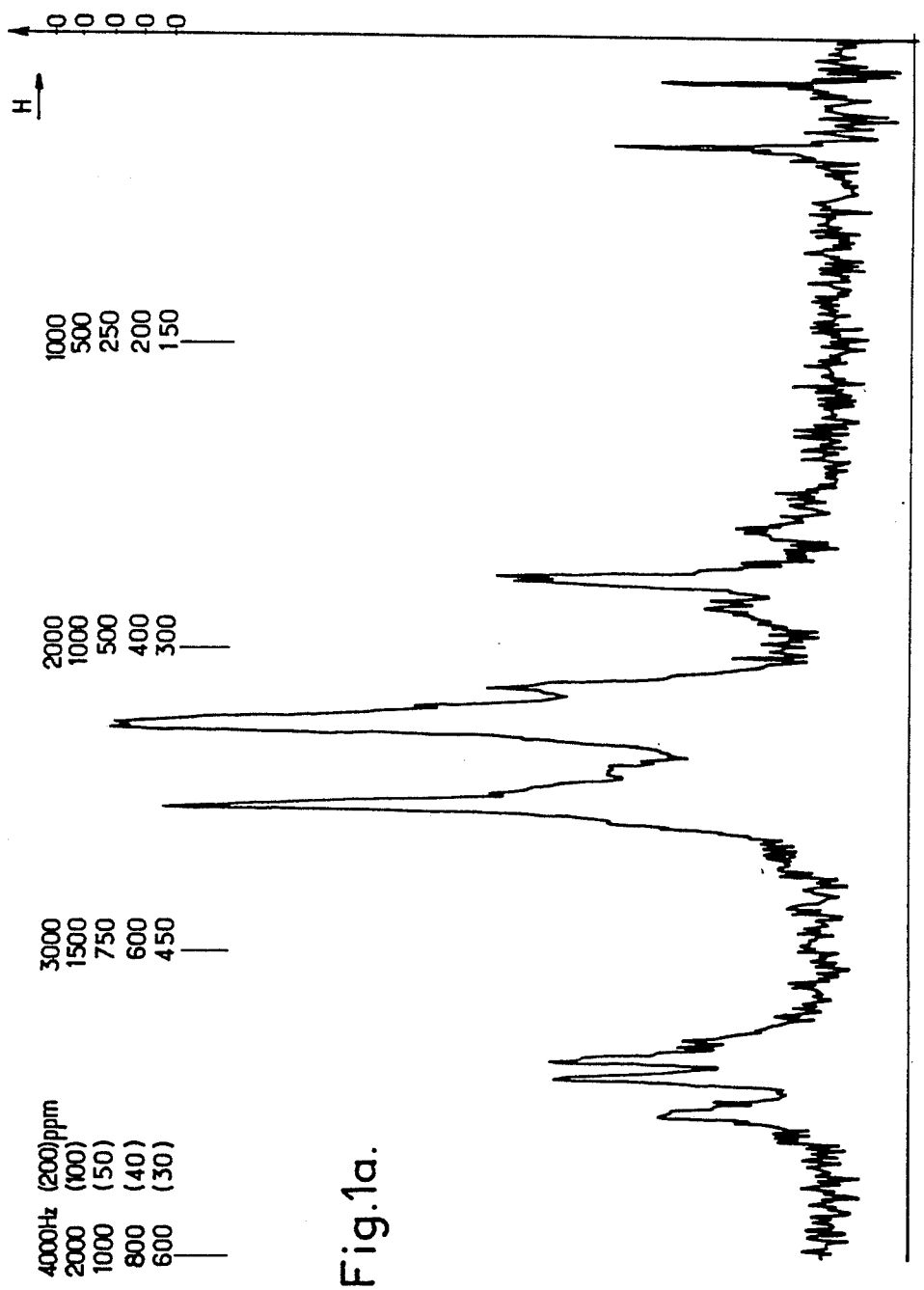
FIG. 1a is the NMR spectrum of a mucopolysaccharidic fraction according to the invention.
Figure 3:
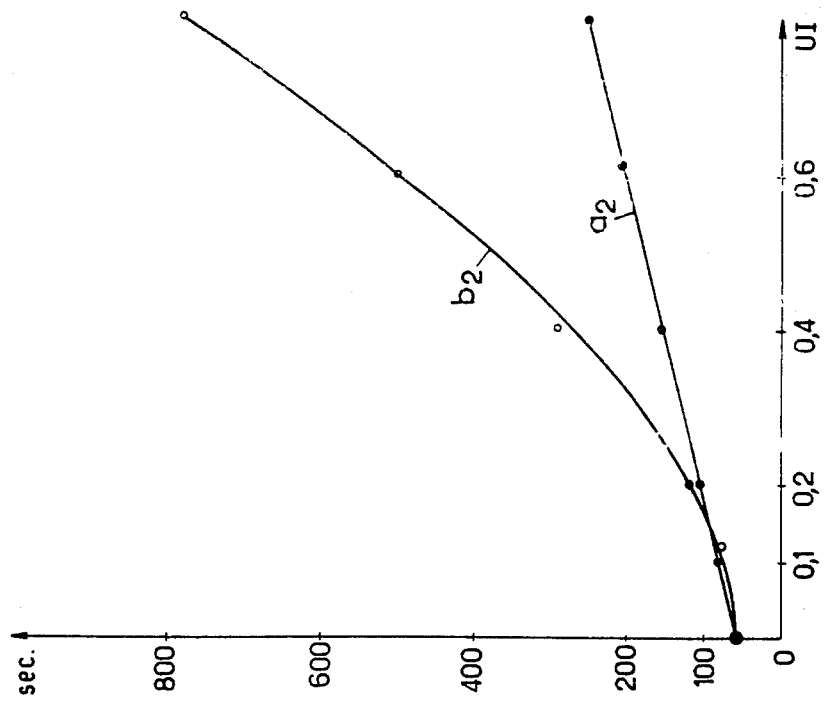
Figure 2:
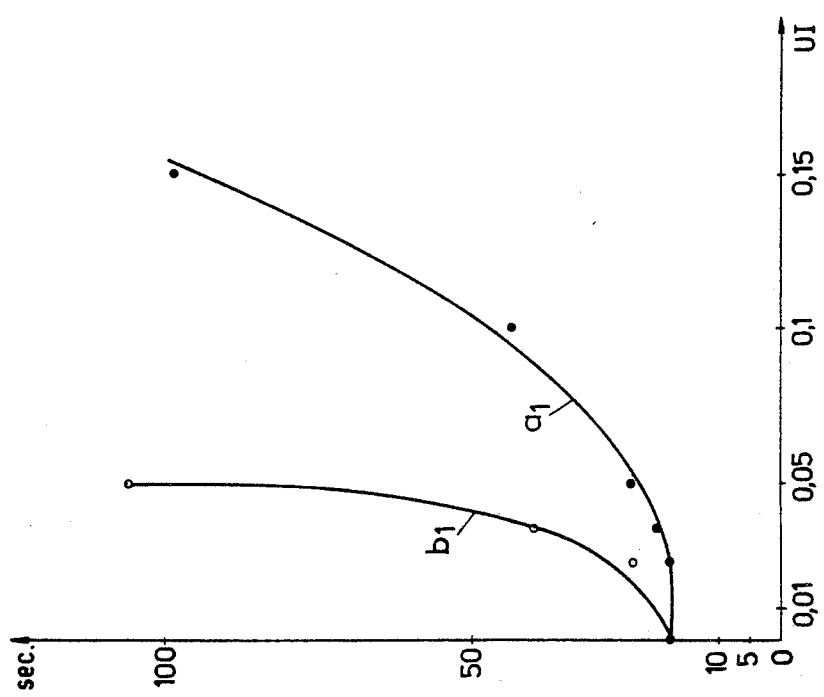

The $^{13}$C spectrum was recorded oon solutions of this fraction dissolved in deuteriated water with a radiation of 20 MHz (see FIG. 1a).

The typical signals observed are the followings:
23.4 ppm: CH$_3$ of NH-acetyl group
54.7 ppm: carbons in position 2 of the acetylated glucosamine moieties
59.2 and 58.8 ppm: carbons in position 2 of the sulfate glucosamine moieties (splitting).
61.7 ppm: carbons in position 6 with —OH groups
67.4 ppm: carbons in position 6 with —O-sulfated groups
98.3** ppm: carbons in position 1
100.00 ppm**: carbons in position 1 of the sulfated iduronic acid units
≃103 ppm: carbons in position 1 of the glucuronic acid units.

(4°) Electrophoretic analysis

The electrophorogram (cellulose acetate, HCl) consists of two bands, both in the heparin region. EXAMPLE II The raw material used was derived from sub-fractions such as are obtained in the purification of commercial heparin, for the production of injectable heparin. It is obtained notably in part from the supernatant liquor obtained by the addition of 0.6 to 0.7 volume of 100° GL alcohol to an aqueous solution of heparin containing 10 to 20 g per liter of sodium chloride, the precipitated purified heparin then being recovered for purification. The raw material used here also contained various heparin purification residues, notably those obtained by alcoholic precipitations, for freeing injectable heparin from traces of inorganic salts.

To 10 kg of this raw material is added 30 volumes of 58° GL (300 liters) of alcohol. The suspension is subjected to vigorous dispersion and agitation for 15 minutes, the stirring being further maintained energetically for 12 hours. It is then left to stand for 48 hours, in order to produce precipitation of the non-solubilized raw material. The slightly cloudy supernatant liquor is taken up again and clarified by centrifugation.

To the supernatant liquor (volume of 280 liters) is added 10 liters of a saturated solution of sodium chloride, and then 1 volume (280 liters) of 100° GL alcohol. The precipitate obtained, which contains the mucopolysaccharide fraction, is washed with 100° GL alcohol, and then dried.

660 g of a fraction are obtained whose Yin-Wessler and USP titers respectively are already in a ratio higher than 2 (fraction P194HH$_{(A)}$).

A supplementary fractionation is then made from this fraction, by dissolving the 660 g fraction in 13,200 ml of water.

To the solution formed is added 264 g of sodium chloride, and then 1.5 volumes of 100° GL alcohol (19.8 liters). The precipitated product is collected, washed with alcohol, then dried. 640 g of the P194HH$_{(C)}$ fraction are obtained, having the following characteristics:
USP titer: 31 IU/mg,
Yin-Wessler titer: 100 U/mg.

The supernatant liquor contained also active mucopolysaccharide fractions (their recovery is described in Example IV).

The P194HH$_{(C)}$ fraction contains also a relatively large amount of substances of high molecular weight mainly heparitine-sulphates, without anticoagulant activity, both in the USP test and in the Yin-Wessler test.

After redissolving in a 0.5M NaCl, 0.1M tris-HCl buffer at pH 7.5, in the proportion of 50 mg/ml, a gel-filtration follows of a volume of 150 ml of the solution on AcA44, in a column of diameter of 215 mm, of 1 meter height, with a flow rate of 800 ml/hour. The high molecular weight substances, of which the major portion is heparitine-sulphates passes in the 10 first liters of eluted solution, dead volume not included.

A mucopolysaccharide fraction with higher Yin-Wessler titer, with a ratio of the Yin-Wessler/USP titers of the order of 4 to 8, can be obtained from the next 6 liters of eluate.

EXAMPLE III

This example describes a modification of the processing of the P194HH$_{(C)}$ fraction of Example II. After it being dissolved again in a 0.5M NaCl, 0.1M tris-HCl buffer at pH 7.5, in a proportion of 50 mg/ml, it is subjected to a gel-filtration on ULTROGEL AcA 44, in a column of 10 cm diameter, 100 cm height. The elution flow rate was 200 ml/hour.

The eluate as collected in successive fractions of 50 ml. The mucopolysaccharide content of each fraction was evaluated as follows: to 1 ml of the fraction was added 2 ml of 100° GL alcohol. After standing for 2 minutes, the turbidity of te mixture was measured at 660 nanometers, on a spectrometer (optical density measurements). This turbidity was directly proportional to the mucopoly-saccharide content of the tested solution.

The C10 fraction, contained in the last third of the fourth liter of eluate, dead volume not included, was collected. The ratio of the Yin-Wessler/USP titers of the C10 fraction was 50/6.

EXAMPLE IV

The final supernatant liquor of Example II is itself supplemented with 19.8 liters of 100° GL alcohol and the suspension formed allowed to stand for 24 hours.

The precipitate formed was collected, washed with 100° GL alcohol and dried. 6 g were obtained of a fraction called P194HH$_{(P)}$ having the following characteristics:
USP titer: 7 IU/mg,
Yin-Wessler titer: 46 U/mg.

EXAMPLE V

The P194HH$_{(P)}$ fraction was again dissolved in a 0.5M tris-HCl, 30 g/l NaCl buffer at pH 7.5, in the proportion of 50 mg/ml.

The solution was subjected to gel filtration on an ULTROGEL AcA 44 column (Pharmacia K 100/100, volume: 7 liters; height 100 cm; diameter 10 cm) with a flow rate of 200 ml/hour.

The elution diagram obtained is shown diagrammatically in FIG. 1, showing the variations in the content of material (optical density DO measured at 660 nanometers) as a function of the eluted volume, in liters (1).

There was collected, after passage of a volume of liquid corresponding to the dead volume of the column, successive fractions K, J, I, G, F, E, D, C, B and A, whose volumes are indicated by the length of the corresponding abscissae segments of FIG. 1.

Each of these fractions possess analytical characteristics which are shown in the following table.

TABLE I

| Characteristics of the Fractions Obtained | | | | |
|---|---|---|---|---|
| Fraction No. | Weight (mg) | USP titer (IU) | Anti-Xa titer(U) | $\frac{\text{Anti-Xa}}{\text{USP}}$ ratio |
| A | 120 | 3.7 | 44.4 | 12 |
| B | 120 | 4.5 | 72 | 16 |
| C | 250 | 6 | 54 | 9 |
| D | 150 | 9 | 135 | 15 |
| E | 300 | 9 | 144 | 16 |
| F | 400 | 11 | 143 | 13 |
| G | 300 | 11.5 | 161 | 14 |
| H | 200 | 13 | 143 | 11 |
| I | 50 | 13 | 91 | 7 |
| J | 200 | 7 | 14 | 2 |
| K | 3500 | 0 | 0 | / |

It is observed that the fractions can be grouped into four types:

(a) The Fractions A, B, C whose elution volumes corespond, in the above-described operational procedure, essentially to the fourth liter eluted, whose USP titers are less than 10 and Yin-Wessler titers less than 80; their molecular weights are at the most of the order of 4,000;

(b) The fractions D, E, F, G, H, whose USP titers are less than 10 and Yin-Wessler titers very high: 135 to 161 units; these fractions also have the most favorable Yin-Wessler/USP titer ratios, from 13 to 16; they are essentially contained in the third liter of eluate; their molecular weights are of the order of 4,000 to 10,000, notably from 4,000 to 8,000;

(c) The fractions I and J, whose ratios of Yin-Wessler/USP titers tend to become unfavorable, and which are probably already contaminated with the K fraction below and (d) The K fraction, containing again essentially heparane-sulphates devoid of anticoagulant activity.

In Table II are displayed the molecular weights of certain of the fractions estimated according to the retention time measured in gel-permeation, by reference to those of the abovesaid polystyrene-sulphonates of known molecular weight. The fraction F is characterized by a main peak corresponding to a retention time of 6.6 minutes and by a shoulder corresponding to a retention time of 6.1 minutes, which testifies to the presence of a constituent whose molecular weight is situated towards 7,200 in the reference system concerned.

The measurements were done by gel-permeation (by means of a SPECTRAPHYSICS 3500 chromatograph), on columns (250×9 mm) filled with silica of granulometry 10–100 microns, notably those marketed under the name LICHROPHOSPHER, of solutions of these fractions in a 0.02M Na$_2$SO$_4$ buffer in the proportion of 1.3 mg of mucopolysaccharide material/ml (volume initially deposited on the column: 50 μl) and with an elution flow rate of 3 ml/minute. The detection of the material was done by UV spectrophotometry (200 mμ).

TABLE II

| Product | Retention time (minutes) | Molecular weights relative to polystyrenes |
|---|---|---|
| P194HH$_{(A)}$ | 7.0 | 2,600 |
| P194HH$_{(B)}$ | 6.9 | 2,900 |
| P194HH$_{(C)}$ | 6.8 | 3,300 |
| P194HH$_{(F)}$ | 6.6 | 4,100 |
| P194HH$_{(F)}$ | 6.1* | 7,200* |
| polystyrene-sulphonate (1) | 6.6 | 4,000 |
| polystyrene- | 6.2 | 6,500 |

TABLE II-continued

| Product | Retention time (minutes) | Molecular weights relative to polystyrenes |
|---|---|---|
| sulphonate (2) polystyrene-sulphonate (3) | 5.4 | 16,000 |
| polystyrene-sulphonate (4) | 4.7 | 31,000 |

*shoulder

EXAMPLE VI

Raw Material

It is formed of byproducts derived from the manufacture of injectable calcium heparinate from crude heparins, such as those extracted from animal tissues (notably intestinal mucous or beef or pork lungs). follows had the following characteristics:
Weight: 252 kg USP titer: 82 IU/mg Yin-Wessler titer: 100 IU/mg.

The processing steps described below were then resorted to.

Extraction with 58° GL alcohol

The 252 kg of raw material were dispersed in 6,000 liters of 58° GL alcohol with vigorous stirring.

The insoluble phase was separated by decantation and centrifugation.

The soluble fraction was recovered by the addition of NaCl and 100° GL alcohol.

There was obtained:
Insoluble fraction: 230 kg recycled in manufacture,
Soluble fraction: 20.6 kg (USP titer=21 IU/mg Yin-Wessler titer=90 IU/mg).

The extraction of the fraction of low molecular weight from the fraction

The fraction soluble in 58° GL alcohol was dissolved in 512 liters of water (20 volumes).

10.24 kg of NaCl were added and then 1.5 volumes of 100° GL alcohol, namely 768 liters. The precipitated fraction was collected, dehydrated with alcohol and dried.
Weight: 19 kg USP titer: 22 IU/mg Yin-Wessler titer: 89 U/mg.

This fraction was put aside and subsequently purified and converted into an injectable calcium salt.

The supernatant liquor from the precipitation at 1.5 volumes was supplemented with 1.5 volumes of alcohol, namely 768 liters. The fraction precipitated was collected, dehydrated with alcohol and dried.
Weight: 700 grams USP titer: 6 IU/mg Yin-Wessler titer: 40 U/mg.

This fraction of 700 grams was a mixture of low molecular weight MPS, little sulphated high molecular weight MPS and more or less degraded nucleic acids.

Removal of the nucleic acids from the low molecular weight fraction

The major part of the nucleic acids was removed by precipitation with manganese chloride, in the following manner:

The fraction of 700 grams was dissolved in 7 liters of water. 1 liter of 10% $MnCl_2$ was added with stirring. The considerable precipitate formed (constituted by the insoluble manganese salts of the RNA and DNA) was removed by centrifugation. The MPS was recovered from the clear supernatant liquor by precipitation with alcohol.
Weight: 480 grams USP titer: 8 IU/mg, Yin-Wessler titer: 54 U/mg.

Isolation of the fractions of very low molecular weights by gel-filtration

The very low molecular weights were separated by gel-filtration on ULTROGEL AcA 44.

A column of 200 mm diameter and 1 m height enabled 25 grams to be treated.

Figure 8:
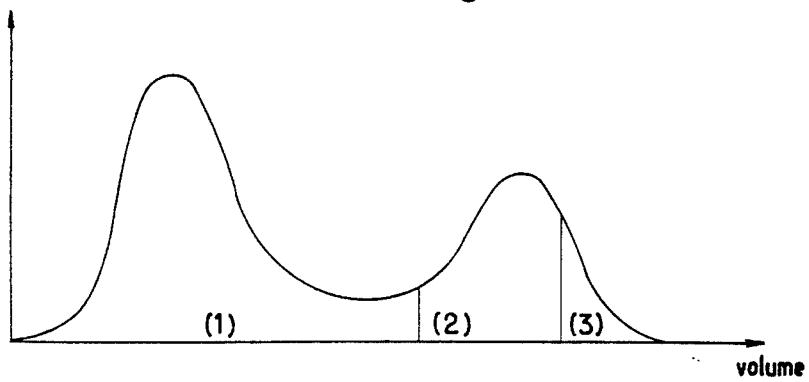
FIG. 8 is a diagrammatic elution diagram of a fraction according to the invention, on the practising of the process, also according to the invention, of selective separation of said fraction from a fraction also containing other constituents.
Figure 9:
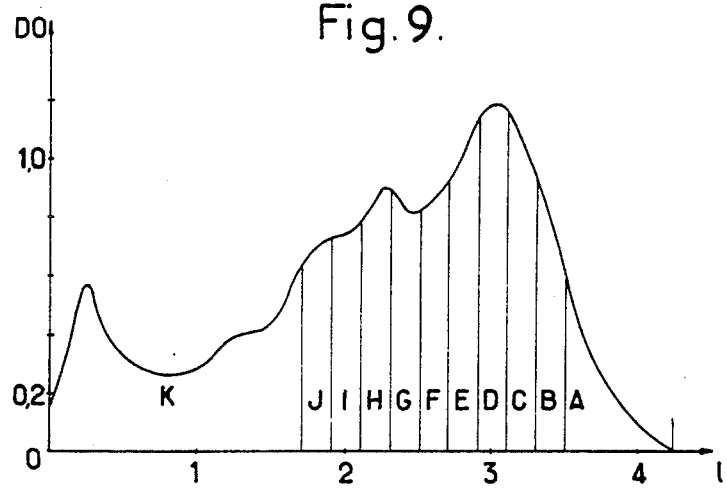
FIG. 9 is representative of an elution diagram characteristic of another preferred mucopolysaccharide fraction, according to the invention.

The elution diagram is of the type shown in FIG. 8.

Three fractions (numbered from (1) to (3)) were collected. They had the following characteristics (for 25 grams applied at the start):
(1) weight: 16 grams USP titer: 12 IU/mg Y.W. titer: 30 U/mg,
(2) weight: 7 grams USP titer: 6.5 IU/mg Y.W. titer: 70 U/mg,
(3) weight: 2 grams USP titer: 2.1 IU/mg Y.W. titer: 60 U/mg.

Chromatography on insolubilized antithrombin III

The preceding fraction (3) was subjected to chromatography on antithrombin III fixed on agarose.

A column of 100 ml used at present enabled 700 mg of the fraction (3) to be treated.

The absorption was effected in an 0.2M NaCl, 0.05M tris-HCL buffer at pH 7.5.

The elution was carried out by a 2M NaCl, 0.05M tris-HCL buffer.

The unfixed portion (600 to 650 mg) had a USP titer close to 1 to 2 IU/mg and a Yin-Wessler titer from 10 to 20 U/mg.

The fixed portion (10 to 30 mg) had a USP titer from 10 to 20 IU/mg and a Yin-Wessler titer from 1000 to 1400 U/mg.

EXAMPLE VII

The fractions A, B and C for Example V hereabove were pooled into a single fraction which was then subjected to an additional fractionation by selective fixation on an agarose-antithrombin III column, under the conditions defined in Example VI.

The fixed fraction was eluted. The fraction named below P194HPA was obtained. It possessed a Yin-Wessler titer of 310 U/mg and a USP titer of 40 IU/mg.

In the same way the above-mentioned fractions E and F of Example V were pooled. The separation procedure of the most active fractions by the technique of fixation-elution defined above, by means of the agarose-antithrombin III column, was resorted to again. Finally there was obtained a fraction P194HHPF having a Yin-Wessler titer of 900 U/mg and a USP titer of 82 IU/mg.

The said fractions P194HHPA and P194HHPF were subjected to NMR analysis, for the $^1H$ proton. The same was done with a conventional heparin (7021HH).

The analysis was carried out on each of the said products, previously dissolved in deuteriated water in the proportion of 14 to 62 mg/0.35 ml, with a BRUKER apparatus, 270 MHz, equipped with a FOURIER transform system and enabling the storage of accumulating spectra. The chemical displacements were measured with reference to TSP, as indicated above.

Figure 10:
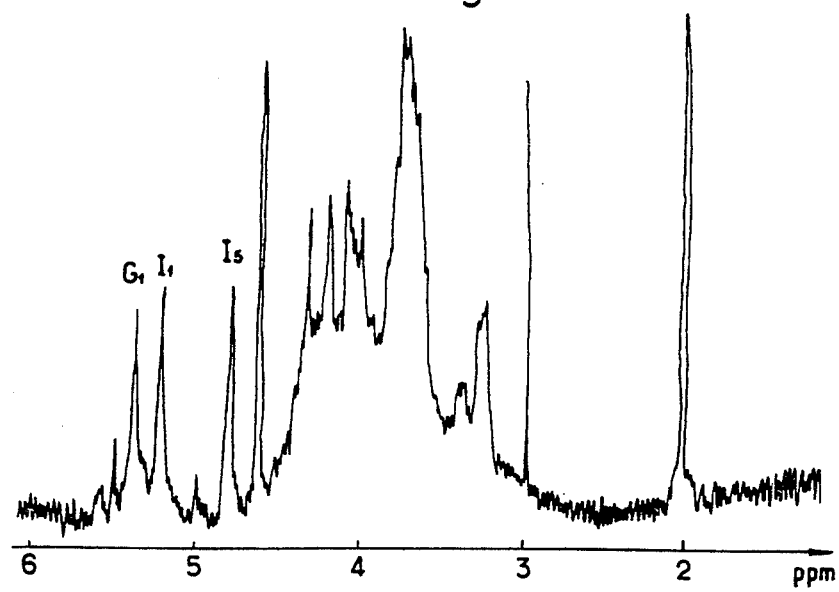
FIG. 10 is the NMR spectrum of a conventional heparin for the $^1$H proton.
Figure 11:
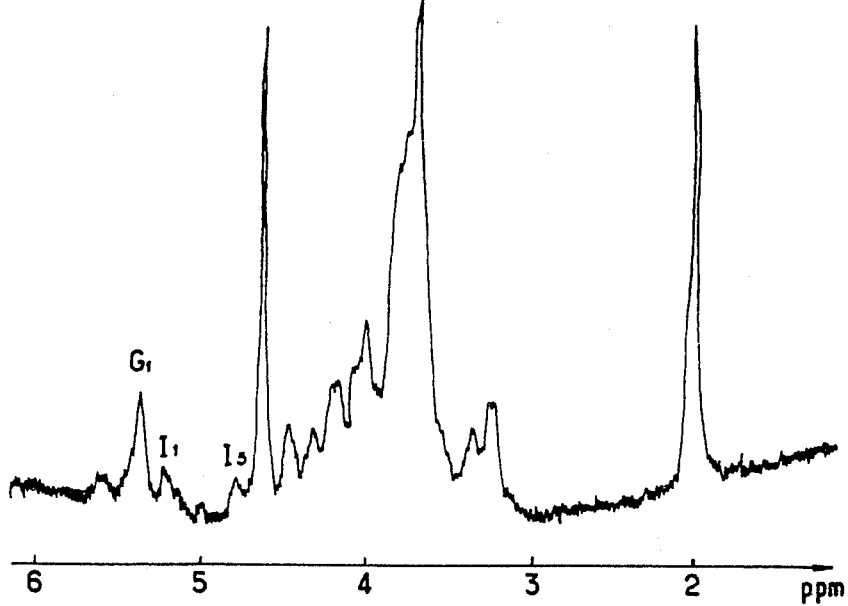
FIGS. 11 and 12 are NMR spectra for the $^1$H proton of different fractions according to the invention.
Figure 12:
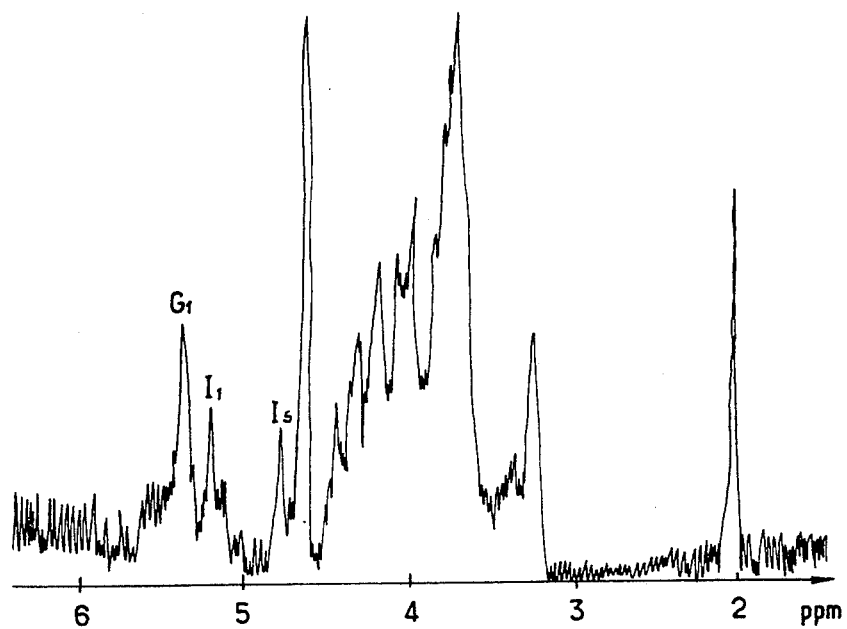

FIG. 10 is representative of the NMR spectrum obtained with conventional heparin. FIGS. 11 and 12 are in the same way representative of the NMR spectra of fractions P 194HHPF and P 194HHPA.

It is noted, by comparison of the NMR spectra, that the $(I_1)$ and $(I_5)$ signals of the fractions according to the invention are distinctly less intense than the signal $(G_1)$, whereas these signals are substantially of the same intensity in the heparin reference spectrum.

EXAMPLE VIII

By applying the techniques described in Examples VI and VII to other starting materials, there were obtained similarly fractions:

| | | |
|---|---|---|
| P 219 HH: | USP titer | = 14 IU/mg |
| | Yin-Wessler titer | = 1350 U/mg |
| P 225 HH: | USP titer | = 17 IU/mg |
| | Yin-Wessler titer | = 1320 U/mg |
| P 231 HH: | USP titer | = 16.2 IU/mg |
| | Yin-Wessler titer | = 1400 U/mg |
| P 194 HH A: | USP titer | = 82 IU/mg |
| | Yin-Wessler titer | = 900 U/mg |
| P 242 HH A: | USP titer | = 16 IU/mg |
| | Yin-Wessler titer | = 1800 U/mg |
| P 255 HH A: | USP titer | = 36 IU/mg |
| | Yin-Wessler titer | = 2145 U/mg |

Figure 13:
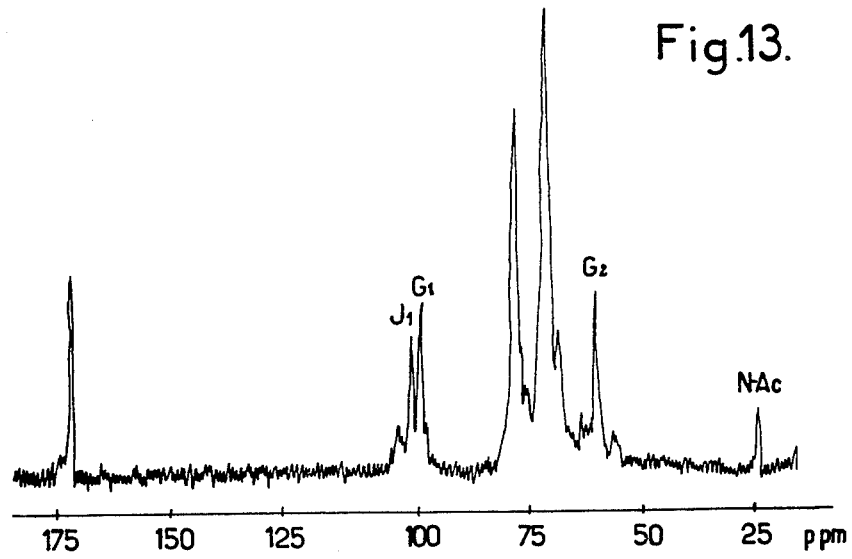
FIG. 13 is an NMR spectrum for the 13 carbon of a conventional heparin used as a comparison.
Figure 14:
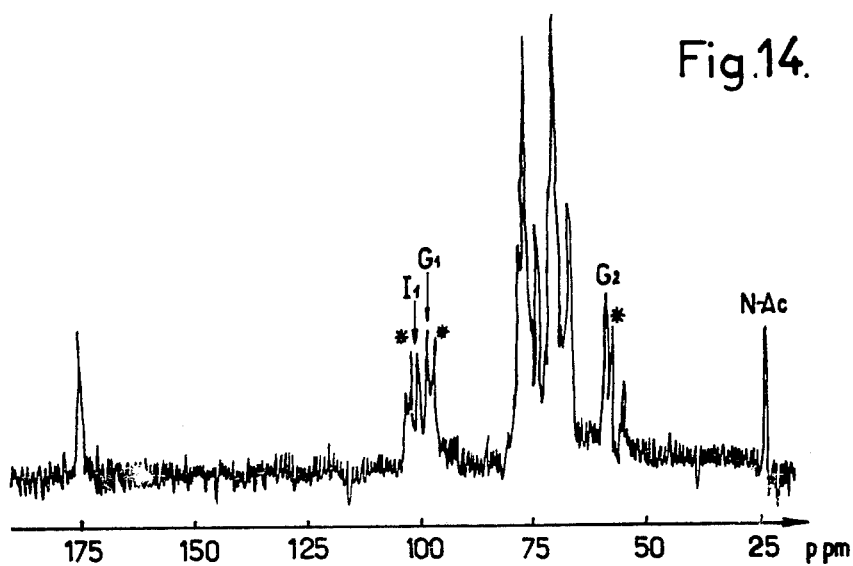
FIG. 14 is an NMR spectrum for the carbon 13 of a fraction according to the invention.
Figure 15:
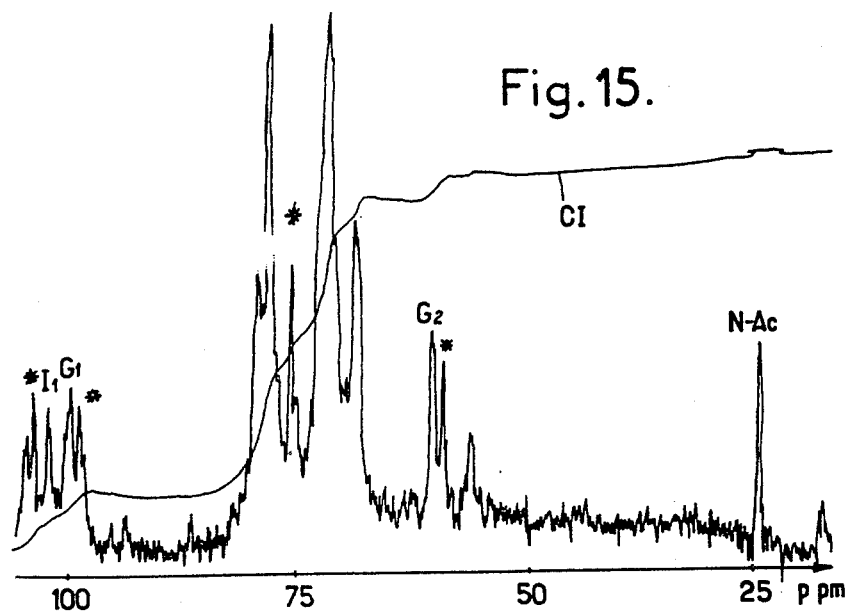
FIG. 15 is an enlargement of a part of the NMR spectrum of FIG. 14.

The P 242HHA fraction was subjected to NMR analysis, for the 13 ($^{13}$C) carbon (FIGS. 14 and 15). The same was done with conventional heparin of reference 7071HH (FIG. 13). The analysis was carried out on each of the fractions (in solution in deuterated water in the proportion of 100 mg in 1 ml of $D_2O$ with a VARIAN CFT-20, 20 MHz apparatus, equipped with a FOURIER transform system (reference for the measurement of chemical displacements: TMS).

There is observed:

the absence practically of a resonance signal characteristic at the presence of OH groups on the primary carbon (in the 6 position of the glucosamine units contained in the mucopolysaccharide fractions of the invention), additional signals (not contained in the NMR spectrum of the reference heparin in the region of the $(I_1)$ and $(G_1)$ signals, in regions corresponding to chemical displacements of the order of 100 ppm, a supplementary signal in the 60 ppm region close to the $(G_2)$ signal, the presence of a resonance signal in the 75 ppm region (to which normally no resonance signal corresponds in the NMR spectra produced under similar conditions with conventional heparin), (the indications of chemical displacements indicated above are evaluated with respect to the $CH_3$ of the N-acetyl glucosamine groups contained in the MPS according to the invention (region of 25 ppm in the spectra of FIGS. 14 and 15).

Signals particular to the fractions or compounds according to the invention are marked with an asterisk in FIGS. 14 and 15.

FIG. 15 also includes the CI integration curve, which enables it to be observed that:

the compound studied was homogeneous, hence practically pure, it has the characteristics of a decasaccharide, it includes one N-acetyl glucosamine unit, for two units of 2-O-sulphate iduronic acid and for two N-sulphate-glucosamine units.

The invention hence enables the preparation of mucopolysaccharide fractions with high anti-Xa activity and having with respect to the Xa factor a remarkable selectivity in the framework of successive enzymatic reactions which characterize the coagulation process.

This remarkable activity and selectivity are also illustrated by the results of the pharmacological tests described below, which were carried out with the P188CH fraction, obtained after the conversion of the P194HHC fraction of Example II, which was in the sodium salt form, into the calcium salt form, by the above-recalled process.

These results are illustrated by the curves of FIGS. 2 to 7, which are all intended to show the comparative anticoagulant effects of the mucopolysaccharide fraction of the invention, on the one hand, and of a conventional heparin (170 USP units/mg), on the other hand.

The curves of FIGS. 2 to 5 are illustrative of the variation observed in vitro of the coagulation times induced in human blood plasmas by increasing doses of a conventional heparin on the one hand, and of the P188CH fraction, on the other hand (the tests corresponding to FIGS. 4 and 5 having been carried out on plasmas free of platelets and consequently impoverished in factor XI).

Figure 6:
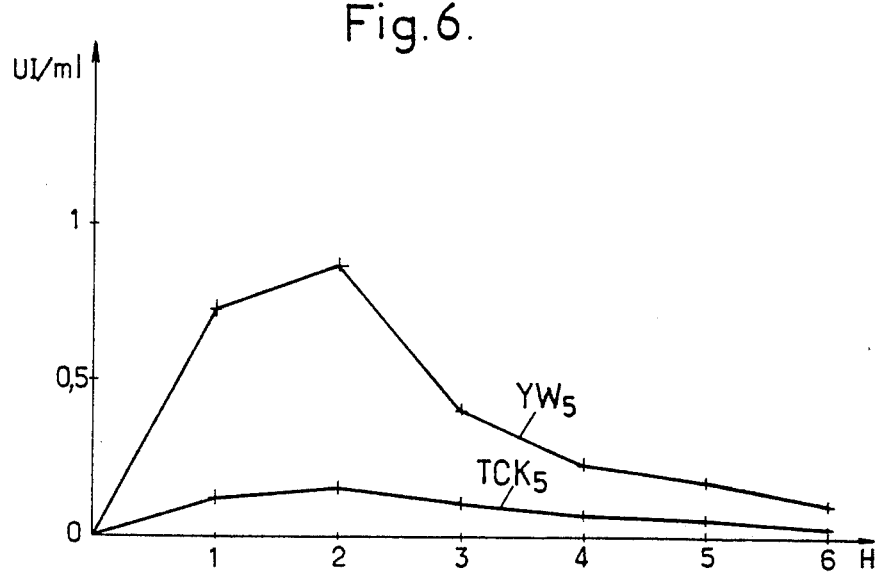
Figure 7:
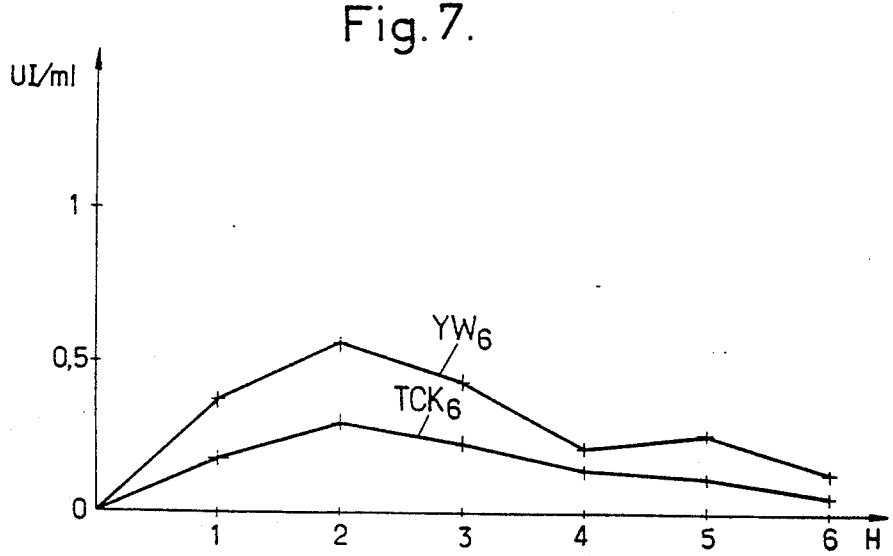

FIGS. 6 and 7 relate to the comparative results obtained in vivo in the rabbit, with the same P188CH fraction (FIG. 6) and the reference heparin (FIG. 7) (average of the results obtained on groups of five rabbits). Each of the rabbits had received 500 Yin-Wessler units per kg of the composition to be tested.

Concerning firstly FIGS. 2 to 5, they show the variations of the times (in seconds):

of thrombin (FIG. 2), of cephalin-kaolin (FIG. 3), of coagulation in the presence of concentrated thromboplastin (FIG. 4) and of diluted thromboplastin (FIG. 5), induced respectively by the preparations studied, namely the mucopolysaccharide fraction (curves $a_1$, $a_2$, $a_3$ and $a_4$) and the reference heparin (curves $b_1$, $b_2$, $b_3$ and $b_4$) as a function of the respective doses used, all expressed in USP units/ml.

The thrombin time and the cephalin-kaolin time both constitute types of measurement reflecting rather the action of the preparations studied respectively on the inhibition of the activated factor II and the overall coagulation. The curves of FIGS. 2 and 3 clearly show in this respect that the mucopolysaccharide fraction according to the invention exerts a distinctly lesser effect than that of the heparin of comparison on the inhibition of the inactivation of a prothrombin and at the level of the overall coagulation. In contrast, FIGS. 4 and 5, which are representative of the phenomena more directly connected with the sequence of enzymatic reactions characteristic of extrinsic coagulation (notably in the relative absence of the factor IIa) show a distinct advantage of the mucopolysaccharide fraction of the invention with respect to the reference heparin. The MPS fraction causes under these conditions a slower coagulation of the blood specimen.

In FIG. 6, there are shown the variations of the activities measured in a rabbit which has received 500 Yin-Wessler units of a mucopolysaccharide fraction of the invention, as a function of time, expressed in hours. To evaluate these activities, recourse is had to the variation of the Yin-Wessler titers (curve $YW_5$) and the cephalin-kaolin titers (curve $CKT_5$) (IU/ml plasma) as a function of time in hours (H).

The same measurements were carried out with the reference heparin. The corresponding variations of the activities studied are illustrated by curves $YW_6$ and $CKT_6$ of FIG. 7.

If FIG. 6 is examined, it is observed that the administration of 500 Yin-Wessler units of the mucopolysaccharide according to the invention causes a considerable anti-Xa activity, compared with the overall coagulability effect, expressed in CKT units, which remains relatively low. It is noted, for example, that at the second hour, the Yin-Wessler activity is 0.85 U/ml, whilst the CKT activity is only 0.15 IU/ml. To the contrary 500 Yin-Wessler units/ml of reference heparin induce an effect expressed by the CKT titers, which is distinctly greater relative to the anti-Xa activity measurable by the Yin-Wessler titer. In particular, it is noted that at the second hour, the anti-Xa activity corresponds to 0.55 U/ml, and that the overall anticoagulant activity, CKT, is of 0.38 IU/ml. The difference between the two titers is hence much smaller than in the case of the mucopolysaccharide according to the invention. The ratio of the Yin-Wessler titer to the CKT titer hence passes from a value less than 2 for the reference heparin to a value greater than 5 for the mucopolysaccharide fraction of the invention.

In vitro and in vivo tests are hence both in the sence of a distinctly more selective action of the mucopolysaccharide fraction of the invention, notably at the level of inhibition of the Xa factor, than that of the reference heparin.

The mucopolysaccharide fractions according to the invention are free of toxicity. The administration of 10,000 U/kg (Yin-Wessler titer) of any of the fractions according to the invention causes in the rabbit neither any toxic reaction nor any pyrogenic effect in the pyrogenicity test in the rabbit according to the French Pharmacopoea.

The invention hence relates more particularly to mucopolysaccharide fractions of the type which have been described, having notably an activity of at least 40, preferably at least 50, and even more advantageously again of at least 100 U/mg (Yin-Wessler titer). Fractions containing more than 300, particularly more than 900 U/mg (Yin-Wessler titer) are even more preferred. It relates also to pharmaceutical preparations, having similar activities, devoid of pyrogenic substances, and in association with pharmaceutical excipients. It relates in particular to the injectable, sterile, concentrated solutions of these fractions, useful in therapeutics, for the control of blood coagulation, which solutions contain from 1,000 to 100,000 U (Yin-Wessler)/ml of the mucopolysaccharide fraction, preferably from 5,000 to 50,000, for example 25,000 U/ml, when these solutions are intended for sub-cutaneous injection or containing again, for example, from 500 to 10,000, for example 5,000 U units/ml of the mucopolysaccharide fraction, when they are intended for intravenous injection or for perfusion.

The mucopolysaccharide fraction according to the invention is advantageously in the form of a salt of at least one physiologically acceptable metal, such as sodium and/or calcium. Advantageously, these pharmaceutical proportions are presented in the form of syringes usable only once, ready for use at any suitable time.

The compositions according to the invention are particularly adapted to the control (preventive or curative) of the blood coagulation in man or animal, notably in those cases where the host is subjected to risks of hypercoagulability, more particularly those resulting from disturbance of the abovesaid extrinsic phase, for example, as a consequence of the release by the organism of thromboplastin, for example, of tissular thromboplastin (surgical operations, atheromatous processes, tumor development, disturbances of the coagulation mechanisms by bacterial or enzymatic activators, etc.). For the sole purpose of illustrating the invention, and without there being discoverable therein cause for limiting the protection of the invention, there will be indicated below, by way of example, a posology capable of being used in man: it comprises for example, the administration to the patient of 1,000 to 25,000 U by the sub-cutaneous route, 2 to 3 times daily, according to the level of hypercoagulation risk or the thrombotic condition of the patient, or from 1,000 to 25,000 U per 24 hours by the intravenous route, in discontinuous administration at regular intervals or continuously by perfusion, or again from 1,000 to 25,000 U (three times weekly) by the intramuscular route (titers expressed in Yin-Wessler U). The doses should naturally, be adjusted in each patient according to the results of previously effected blood analyses, the nature of the disorder from which the patient is suffering and, generally, his state of health, as is well known.

The invention again also relates to the application of the mucopolysaccharides according to the invention to the constitution of biological reactant usable in laboratory, notably as a comparison reference for the study of other substances of which the anticoagulant activity is to be tested, notably at the level of inhibition of the factor Xa.

As is self-evident and as emerges already from the foregoing, the invention is in no way limited to those of its types of application and embodiments which have been more especially envisaged; it encompasses on the contrary all modifications, in particular those in which the aqueous-alcoholic extraction medium defined above is formed by a mixture of water and an alcohol other than ethanol, for example an aliphatic or aromatic alcohol, preferably cyclic or acyclic saturated aliphatic alcohol, such as primary alcohols including 1 to 6 carbon atoms, it being of course understood that there should be determined in each case, by simple routine operations, the proportions of water/alcohol of the medium which lead to an extraction of a mucopolysaccharide fraction equivalent to that which is obtained with a 55°–60° GL water-ethanol mixture.

Finally it is to be noted that all definitions set forth in the claims that follow are whenever appropriate also part of the present disclosure.

We claim:

1. Heparinic mucopolysaccharide fractions which have improved antithrombotic activity in vivo (measured in terms of activity of anti-Xa per milligram), which are more selective with respect to anti-Xa activity than that of heparin and have a lower whole anticoagulation activity than heparin (measured in USP units per milligram), which heparinic mucopolysaccharide fractions have (1) a molecular weight in the range of about 2,000 to 10,000 daltons, (2) are soluble in water-alcohol having a titer of 55°–61° GL, (3) are insoluble in alcohol, (4) have a ratio of anti-Xa titer to USP titer of at least 3, wherein in said heparinic mucopolysaccharides, fractions comprise, (5) glucosamine units which are sulfated in the primary position, (6) one N-acetyl glucosamine unit for two 2-O-sulfate iduronic acid units and for two N-sulfate-glucosamine units, the carbon-13 NMR spectrum in $H_2O$ (at a radiation of 20 MHz) having the following resonance signals (in the stated regions) indicating the presence of the stated atoms:

| | |
|---|---|
| 23.4 ppm: | $CH_3$ of NH—acetyl group, |
| 54.7 ppm: | carbons in position 2 of the acetylated glucosamine moieties, |
| 59.2 and 58.8 ppm: | carbons in position 2 of the sulfate glucosamine moieties (splitting), |
| 61.7 ppm: | carbons in position 6 with —OH groups, |
| 67.4 ppm: | carbons in position 6 with —O—sulfated groups, |
| 98.3$^x$ $^x$ppm: | carbons in position 1, |
| 100.00 ppm$^{xx}$: | carbons in position 1 of the sulfated iduronic acid units, and |
| 103 ppm: | carbons in position 1 of the glucuronic acid units, | and the physiologically acceptable salts thereof.

2. The mucopolysaccharides of claim 1, which have a carbon-13 NMR spectrum as shown in FIG. 1a.

3. The mucopolysaccharides of claim 1, the carbon-13 NMR spectrum of which exhibits glucosamine units, the primary carbons in the 6-position being free of hydroxyl group and exhibiting resonance signals in the region corresponding to chemical displacements in the 100 ppm region (as shown by stars in FIG. 14).

4. The mucopolysaccharides of claim 2, wherein the carbon-13 NMR spectrum exhibits another resonance signal in the 75 ppm region.

5. The mucopolysaccharides of claim 4, which proton NMR spectrum exhibits resonance signals in the 4.8, 5.2 and 5.4 ppm regions,, which signals in the 4.8 and 5.2 ppm regions are weaker than that in the 5.4 ppm region.

6. The mucopolysaccharides of claims 3, wherein the carbon-13 NMR spectrum exhibits a supplementary signal in the 60 ppm region adjoining the $G_2$ designated signal (as shown in FIGS. 14 and 15).

7. The mucopolysaccharides of claim 1, as shown by one of the NMR spectra of FIGS. 11, 12, 14 or 15.

8. The mucopolysaccharides of claim 1, which is selectively fixable on antithrombin III.

9. The mucopolysaccharides of claim 1, which have a USP titer of about 45 units per mg, an anti-Xa titer of about 160 units per mg and a ratio of anti-Xa titer to USP titer of about 3.55.

10. The mucopolysaccharides of claim 1, wherein the USP titer is less than about 10 units per mg and the anti-Xa titer is about 161 units per mg.

11. The mucopolysaccharides of claim 1, wherein the ratio of anti-Xa titer to USP titer is at least 6, and the anti-Xa titer is at least 300 units/mg.

12. The mucopolysaccharides of claim 11, wherein the ratio of anti-Xa titer to USP titer is at least 10.

13. The mucopolysaccharides of claim 12, wherein the ratio of anti-Xa titer to USP titer is at least 50.

14. The mucopolysaccharides of claim 11, wherein the ratio of anti-Xa titer to USP titer is at least 130.

15. The mucopolysaccharides of claim 11, wherein the anti-Xa titer is not less than about 50 units per mg.

16. The mucopolysaccharides of claim 11, wherein the ratio of anti-Xa titer to USP titer is higher than 18 and the anti-Xa titer is at least 900 units per mg.

17. The mucopolysaccharides of claim 13, wherein the ratio of anti-Xa titer to USP titer is higher than 65 and the anti-Xa titer is at least 1300 units per mg.

18. The mucopolysaccharides of claim 1, wherein the USP titer does not exceed about 13 units per mg, the anti-Xa titer is in the range of about 135 to about 160 units per mg, the ratio of anti-Xa units to USP units is in the range of 13 to 16 and the molecular range is from about 4,000 to about 8,000 daltons.

19. The mucopolysaccharides of claim 1, wherein the USP titer does not exceed about 6 units per mg, the anti-Xa titer is not less than about 44 units per mg, the ratio of anti-Xa to USP titers is over about 9 and the molecular weight is in the range of about 4,000 to 8,000 daltons.

20. The mucopolysaccharides of claim 1, wherein the salts are selected from the group consisting of sodium and calcium.

21. A therapeutic composition which comprises a therapeutically acceptable carrier and in an antithrombotic effective amount, the heparinic mucopolysaccharide fractions of claims 1, 2, 3, 4, 5, 6, 7, 8, 9, 10, 11, 12, 13, 14, 15, 16, 17, 18, 19 or 20.

22. The therapeutic composition of claim 21, which has an anti-Xa titer higher than about 100 units per mg.

23. The therapeutic composition of claim 21, which is a solution of the mucopolysaccharides in a concentration of about 1,000 to 100,000 Yin-Wessler units per ml.

24. The therapeutic composition of claim 23, which is a solution of the mucopolysaccharides in a concentration of about 5,000 to about 50,000 units per ml.

25. A therapeutic method for controlling thrombosis in a patient which comprises administering to the patient in a therapeutically antithrombotic effective amount, the composition of claims 21, 22, 23 or 24 and controlling thrombosis by selectively inhibiting the coagulation factor Xa.

26. The therapeutic method of claim 25 wherein the administration of the composition is by injection or infusion.

27. A process for obtaining heparinic mucopolysaccharides which have improved antithrombotic activity in vivo and inhibition of the Xa-factor (measured in terms of anti-Xa activity) more selective than that of heparin and a lower whole anticoagulation activity than heparin (measured in USP units), which mucopolysaccharides have a molecular weight in the range of about 2,000 to 10,000 daltons, a ratio of anti-Xa to USP titers of at least 3, which process comprises mixing heparin mucopolysaccharides having a molecular weight in the range of about 2,000 to 50,000 daltons in a 55°–61° GL aqueous-alcoholic medium, separating the liquid medium which contains mucopolysaccharides in solution and precipitating out the soluble mucopolysaccharides by alcoholic precipitation, said mucopolysaccharides having an increased ratio of anti-Xa titer to USP titer as compared to the starting heparin mucopolysaccharides being defined in claim 1.

28. The process of claim 27, which comprises recovering the alcohol-precipitated mucopolysaccharides, subjecting an aqueous solution of said mucopolysaccharides to gel-filtration and recovering the fraction which has a further increased anti-Xa titer to USP titer ratio as compared to that of the alcohol-precipitated mucopolysaccharides.

29. The process of claims 27 or 28, which comprises the further step of contacting the mucopolysaccharides which have increased anti-Xa titer with antithrombin III on a support, selectively affixing thereon the mucopolysaccharides which have a higher Yin-Wessler activity than the mucopolysaccharides which are not affixed thereon and recovering the affixed mucopolysaccharides by elution, which mucopolysaccharides have further increased anti-Xa titer to USP titer ratio than the starting mucopolysaccharides.

* * * * *